United States Patent
Gujraty et al.

(10) Patent No.: US 10,549,129 B2
(45) Date of Patent: Feb. 4, 2020

(54) COSMETIC COMPOSITIONS AND METHODS PROVIDING ENHANCED PENETRATION OF SKIN CARE ACTIVES

(71) Applicant: The Procter & Gamble Company, Cincinnati, OH (US)

(72) Inventors: Kunal Virendra Gujraty, Singapore (SG); Shikhar Gupta, Singapore (SG); Stevan David Jones, Singapore (SG); Naohisa Yoshimi, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 98 days.

(21) Appl. No.: 15/191,648

(22) Filed: Jun. 24, 2016

(65) Prior Publication Data

US 2017/0367957 A1     Dec. 28, 2017

(51) Int. Cl.
| | |
|---|---|
| *A61K 8/49* | (2006.01) |
| *A61K 8/06* | (2006.01) |
| *A61K 8/34* | (2006.01) |
| *A61K 8/37* | (2006.01) |
| *A61Q 19/00* | (2006.01) |
| *A61Q 19/08* | (2006.01) |
| *A61K 8/67* | (2006.01) |

(52) U.S. Cl.
CPC .............. *A61Q 19/00* (2013.01); *A61K 8/342* (2013.01); *A61K 8/345* (2013.01); *A61K 8/37* (2013.01); *A61K 8/375* (2013.01); *A61K 8/675* (2013.01); *A61Q 19/08* (2013.01); *A61K 2800/5922* (2013.01)

(58) Field of Classification Search
CPC .................................. A61K 8/062; A61K 8/14
See application file for complete search history.

(56) References Cited

U.S. PATENT DOCUMENTS

| | | | |
|---|---|---|---|
| 4,096,240 A | 6/1978 | Mathur | |
| 5,989,529 A * | 11/1999 | Kaplan | ............... A61K 8/046 424/400 |
| 8,097,571 B2 | 1/2012 | Mellul et al. | |
| 9,511,144 B2 | 12/2016 | Jones et al. | |
| 2002/0168329 A1* | 11/2002 | Kini | ................... A61K 8/361 424/70.22 |
| 2006/0204561 A1 | 9/2006 | Muhammad | |
| 2008/0031906 A1* | 2/2008 | Nohata | ................. A61K 8/04 424/401 |
| 2008/0169215 A1 | 7/2008 | Tanaka et al. | |
| 2009/0263340 A1 | 10/2009 | Ille-Boehler | |
| 2011/0110874 A1 | 5/2011 | Tanaka et al. | |
| 2013/0195925 A1 | 8/2013 | Arshed | |

FOREIGN PATENT DOCUMENTS

| | | |
|---|---|---|
| JP | 2003277220 A | 10/2003 |
| JP | 2007001947 A | 1/2007 |
| WO | WO9729735 A1 | 8/1997 |
| WO | WO 02/03952 A2 | 1/2002 |

OTHER PUBLICATIONS

Bissett, et al., Niacinamide: A B Vitamin that Improves Aging Facial Skin Appearance, Dermatologic Surgery; vol. 31:7 Part 2: Jul. 2005, pp. 860-865.
Draelos, Clinical Situations Conducive to Proactive Skin Health and Anti-Aging Improvement, Journal of Investigative Dermatology Symposium Proceedings (2008), vol. 13, pp. 25-27.
International Search Report and Written Opinion of the International Searching Authority, PCT/US2014/071053, dated Mar. 16, 2015, 7 pages.
Maghraby, et al., Mechanisms of action of novel skin penetration enhancers: Phospholipid versus skin lipid liposomes, International Journal of Pharmaceutics, 2005, vol. 305, pp. 90-104, published online Sep. 30, 2005.
Osborne, et al., Skin Penetration Enhancers Cited in the Technical Literature, Pharmaceutical Technology, 1997, pp. 58-66.
Pathan, et al., Chemical Penetration Enhancers for Transdermal Drug Delivery Systems, Tropical Journal of Pharmaceutical Research, Apr. 2009, vol. 8 (2), pp. 173-179.
Suhonen, et al., Chemical enhancement of percutaneous absorption in relation to stratum corneum structural alterations, Journal of Controlled Release, vol. 59 (1999), pp. 149-161.
Trommer, et al., Overcoming the Stratum Corneum: The Modulation of Skin Penetration, Skin Pharmacol Physiol, 2006, vol. 19, pp. 106-121, published online May 9, 2006.
Williams, et al., Penetration enhancers, Advanced Drug Delivery Reviews, vol. 56 (2004), pp. 603-618.
Williams, et al., Penetration enhancers, Advanced Drug Delivery Reviews, vol. 64 (2012), pp. 128-137.
Mintel GNPD Record ID: 866993, Kanebo Cosmetics Freeplus Barrier Repair Cream N, Feb. 2008.

* cited by examiner

Primary Examiner — Kyle A Purdy
(74) Attorney, Agent, or Firm — John G. Powell; S. Robert Chuey

(57) ABSTRACT

A cosmetic composition suitable for topical application is provided. The cosmetic composition comprises: glycerin; a lipid bilayer structurant with a glyceryl headgroup; a penetration enhancer; and a skin care active. The penetration enhancer increases the amount of active that enters skin when the composition is topically applied, while the glycerin and lipid bilayer structurant with glyceryl headgroup work together with lipid bilayers of the skin to impede progress of active through the skin.

4 Claims, 11 Drawing Sheets

COSMETIC COMPOSITIONS AND METHODS PROVIDING ENHANCED PENETRATION OF SKIN CARE ACTIVES

TECHNICAL FIELD

Cosmetic compositions providing enhanced penetration of actives into skin and increased residency time of actives in skin are provided along with methods of use related thereto.

BACKGROUND

Skin care actives, for example the Vitamin B compound, niacinamide, are well known cosmetic skin care agents that are believed to provide a variety of skin care benefits (see, e.g., Bissett el al. "Niacinamide: A B Vitamin that Improves Aging Facial Skin Appearance" and Draelos "Clinical Situations Conducive to Proactive Skin Health and Anti-Aging Improvement"). Some of the reported benefits include improvement in the appearance of facial skin texture, red blotchiness, hyperpigmentation, and the enhancement of skin barrier function. Given these benefits, there is a continuing desire to increase the amount of vitamin B compounds delivered into human skin from topically applied cosmetic compositions to further enhance the skin benefits provided by these compounds. There is also a desire to ensure the skin care active has sufficient time to act on the skin.

It is known that a rate limiting step in the percutaneous absorption of ingredients is their initial penetration into and across the stratum corneum, see, e.g., Suhonen et al., "Chemical Enhancement of Percutaneous Absorption In Relation To Stratum Corneum Structural Alterations", Suhonen et al., Journal of Controlled Release, 59 (1999), pgs 149-161. Suhohen et al. also observed that there are at least two potential pathways through the stratum cornenum: 1) transcellular (i.e., across the corneocytes and the lipid matrix), and 2) intercellular (i.e., via the lipid domains between the corneocytes), with the intercellular route believed to be providing the principal route for the permeation of ingredients.

Skin penetration enhancers are well known. As far back as 1997, a literature review by Osborne et al. purported to find more than 275 chemical compounds cited as enhancing skin permeation (see, e.g., Osborne, David, "Skin Penetration Enhancers Cited in the Technical Literature, Pharmaceutical Technology", 1997, pp 58-66). Compounds identified by Osborne include various species of fatty alcohols, fatty acid esters, fatty acids, fatty alcohol ethers, enzymes, amines and amides, surfactants, n-methyl pyrrolidones, ionic compounds and various others. More recently, Williams et al. noted that "[n]umerous compounds have been evaluated for penetration enhancing activity, including sulphoxides (such as dimethylsulphoxide, DMSO), azones (e.g., laurocapram), pyrrolidones, (for example 2-pyrrolidone, 2P), alcohols and alkanols (ethanol, or decanol), glycols (for example propylene glycol, PG, a common excipient in topically applied dosage forms), surfactants (also common in dosage forms) and terpenes". Williams et al., "Penetration Enhancers", Advanced Drug Delivery Reviews 56, pgs 603-618 (2004), see also, Pathan et al., "Chemical Penetration Enhancers for Transdermal Drug Delivery Systems", Tropical Journal of Pharmaceutical Research, Vol. 8(2), pgs 173-179 (2009).

U.S. patent application Ser. No. 13/803,692 discloses use of the penetration enhancer hexyldecanol in combination with glycerin and a vitamin B active. Glycerin is known to be an important component of skin hydration in topical applications. Niacinamide, which is a vitamin B compound soluble in both water and glycerin, is associated with a variety of cosmetic skin care benefits. Given the cosmetic benefits provided by glycerin and vitamin B compounds, it is often desirable to combine both in cosmetic/skin care compositions. However, it has been observed that the presence of glycerin in such a cosmetic composition can retard the penetration of niacinamide into the skin, when measured over a 6 hour time period. The inventors of U.S. Ser. No. 13/803,692 have surprisingly discovered that introducing a penetration enhancer, e.g. hexyldecanol or other diol, may counteract this effect and, in some instances, enables glycerin to synergistically enhance rather than retard penetration of niacinamide into the stratum corneum.

While various skin penetration enhancers are known, their mechanisms of action, particularly in the stratum corneum, are still being investigated. For example, Suhonen et al. postulated that "many penetration enhancers are capable of inserting between the hydrophobic tails of the bilayer, thus disturbing their packing, increasing their fluidity and, subsequently, leading to easier diffusion of lipid-like penetrants". Suhonen et al. also concluded however that "[a]lthough during the last 10 years an enormous amount of knowledge became available on the structure of the stratum corneum and the effect of solvent and penetration enhancers on this structure, still our knowledge on this tissue and its lipid organization is very limited". Similarly, Williams et al. noted in 2004 that the inclusion of penetration enhancers "into topical or transdermal formulations is limited since the underlying mechanisms of action of these agents are seldom clearly defined". Even more recently, Williams and Barry, "Penetration enhancers", Advanced Drug Delivery Reviews, Vol. 64, pgs 128-137 (2012), stated that "[i]t is difficult to select rationally a penetration enhancer for a given permeant." While the effects of certain individual ingredients on skin penetration has been studied to some degree, the role that these ingredients, or combinations of ingredients, may play in penetration of cosmetic agents through the stratum corneum appears to be less studied or defined.

SUMMARY

A cosmetic composition suitable for topical application is provided. A cosmetic composition suitable for topical application, comprising: glycerin; a lipid bilayer structurant with a glyceryl headgroup; a penetration enhancer; and a skin care active.

A method of using a cosmetic composition of using the composition is also provided. At least one method may comprise applying a cosmetic composition to a facial skin surface in need of treatment, wherein the cosmetic composition comprises glycerin; a lipid bilayer structurant with a glyceryl headgroup; a penetration enhancer; and a skin care active.

A method of increasing the percentage of skin care active retained in skin is also provided. The method may comprise topically applying a cosmetic composition to skin, wherein the cosmetic composition comprises glycerin; a lipid bilayer structurant with a glyceryl headgroup; a penetration enhancer; and a skin care active.

BRIEF DESCRIPTION OF THE DRAWINGS

While the specification concludes with claims, it is believed that the same will be better understood from the following description taken in conjunction with the accompanying drawings in which:

DETAILED DESCRIPTION

Figure 1:
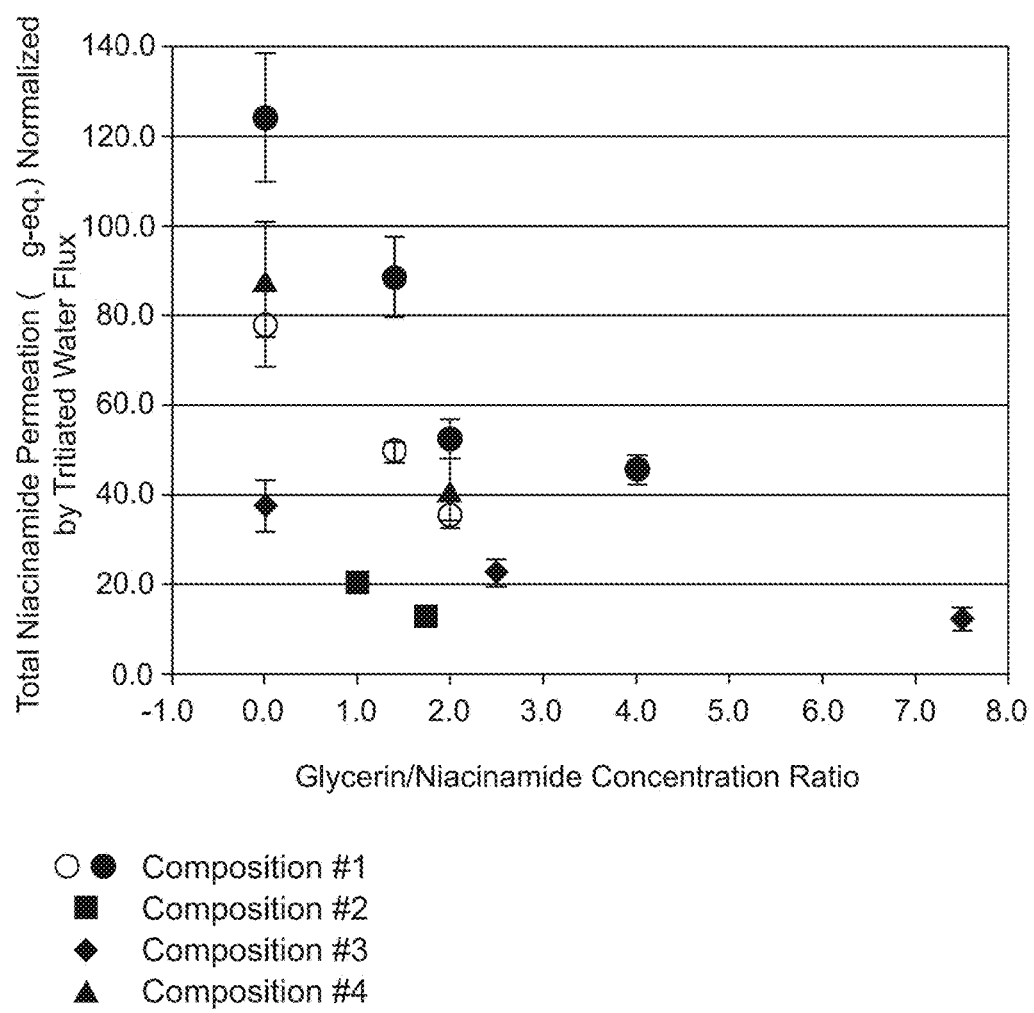
FIG. 1 is a graph of total niacinamide penetration versus glycerin/niacinamide concentration ratio for four cosmetic compositions.

Described hereafter are various embodiments of cosmetic compositions that provide enhanced penetration of actives, e.g. vitamin B compounds, into skin and increase the residency time of the active in skin, particularly in the epidermis and dermis. It is known from U.S. Ser. No. 13/803,692 that combining glycerin with a penetration enhancer, such as hexyldecanol, enhances penetration of a vitamin B compound, such as niacinamide, into skin. It has been surprisingly discovered that it is possible to increase the amount of time the vitamin B compound remains in skin by combining a glyceryl ester or glyceryl ether with glycerin and the penetration enhancer.

As used herein, vitamin B compounds include B1 compounds, B2 compounds, B3 compound, B5 compounds, such as panthenol or "pro-B5", pantothenic acid, pantothenyl; B6 compounds, such as pyroxidine, pyridoxal, pyridoxamine, carnitine, thiamine, and riboflavin. In some embodiments, the vitamin B compound is a B3 compound having the formula:

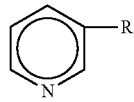

wherein R is —CONH$_2$ (i.e., niacinamide), —COOH (i.e., nicotinic acid) or —CH2OH (i.e., nicotinyl alcohol), derivatives thereof, and salts of any of the foregoing. In some examples, the cosmetic composition may have a concentration of a vitamin B compound, by weight of the cosmetic composition, of between about 0.0005%, 1%, 2%, 3%, 4% or 5% to 6%, 8%, 10% or 11%.

Penetration enhancers are known to alter the physical or chemical nature of the stratum corneum to allow certain things to penetrate this layer to reach the lower layers of skin. As used herein, the term penetration enhancers includes, as an example, fatty acids (e.g. oleic acid, linoleic acid, isostearic acid), undecylenoyl-L-phenylalanine, hexyldecanol (e.g. 2-hexyl-1-decanol), octyl salicylate, isopropyl lauroyl sarcosinate.

As used herein, lipid bilayer structurants are molecules that embed themselves in the skin lipid bilayer to promote the ordering of the bilayers, resulting in improved barrier function and increased skin hydration.

I. IN VITRO OBSERVATIONS RELATING TO A VITAMIN B COMPOUND AND GLYCERIN

Topical application of niacinamide, which is soluble in both water and glycerin, can be associated with a variety of cosmetic skin care benefits. These may include: i) normalization of age associated depletions of nicotinamide coenzymes in skin, ii) up-regulation of epidermal ceramide synthesis with concurrent epidermal barrier benefits, iii) protection against damage produced by UV irradiation, iv) inhibition of the transfer of melanosomes from melanocytes to keratinocytes (thereby providing a potential skin tone benefit), and reduction in sebaceous lipogenesis. These activities may improve the appearance of aging/photo-damaged skin.

Glycerin is a small, polar molecule that is liquid at room temperature and miscible with water. Endogenous glycerin is believed to be an important component of skin hydration and topical application of cosmetic products containing glycerin can be associated with improvements in barrier function, induction of biomarkers associated with keratinocyte proliferation and wound healing, reduction in melanin intensity, increases in epidermal thickness, and improvements in general skin appearance.

Given the cosmetic benefits likely provided by glycerin and vitamin B compounds, it is often desirable to combine both in cosmetic compositions. However, it is has been observed that the presence of glycerin in such a cosmetic composition can retard the penetration of niacinamide into the skin. Referring to Example 1, it has been observed that increasing glycerin concentrations can decrease niacinamide skin penetration from a variety of cosmetic compositions. In Example 1, a series of in vitro skin penetration studies were conducted over a 6 hr time period to assess the impact of glycerin upon the penetration of radiolabeled niacinamide from several cosmetic compositions, including an oil-water emulsion, a water-in-silicone emulsion, and a water gel. The cosmetic compositions were topically applied to split-thickness human cadaver skin. A Franz diffusion cell system was used to measure the amount of penetration of the radiolabeled niacinamide through the cadaver skin. The kinetics of in vitro radiolabeled niacinamide skin penetration were observed at fixed glycerin concentrations, and the impact of glycerin and niacinamide concentrations upon the penetration of radiolabeled niacinamide and glycerin over 6 hours were measured. In addition, niacinamide penetration was measured as a function of glycerin concentration.

Referring to FIG. 1, total niacinamide penetration as a function of the glycerin/niacinamide ratio for the four cosmetic compositions tested in Example 1 are plotted. The data suggests that the addition of glycerin decreases niacinamide penetration from a variety of cosmetic compositions. Further, the data suggests that increasing glycerin concentration incrementally decreases niacinamide skin penetration from a variety of cosmetic compositions.

II. IN SILICO OBSERVATIONS RELATING TO A VITAMIN B COMPOUND AND GLYCERIN

Figure 2:
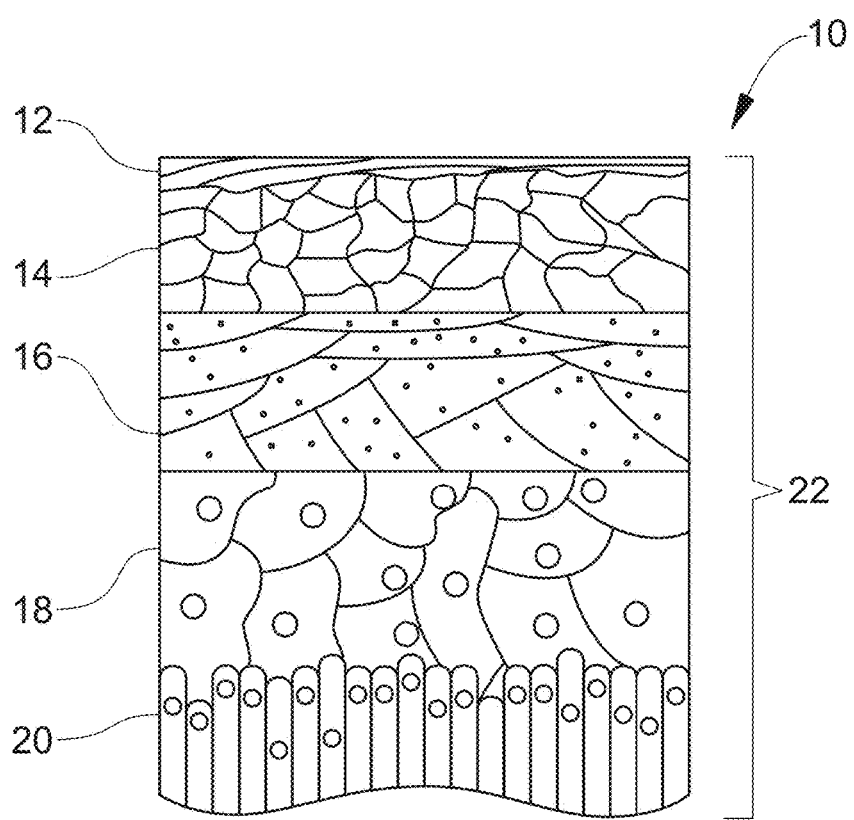
FIG. 2 is a schematic representation of the epidermal and dermal layers of human skin.
Figure 3:
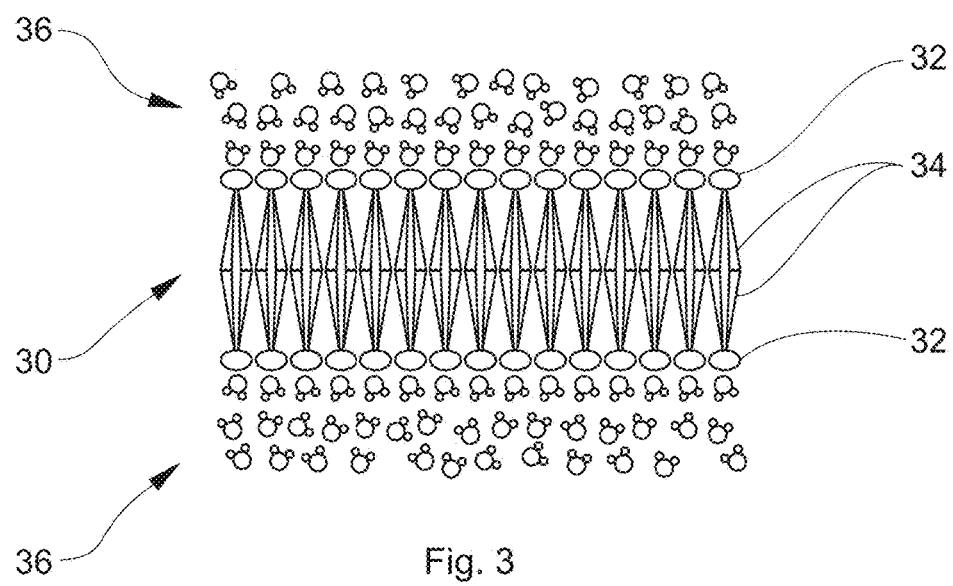
FIG. 3 is a schematic representation of lipid bilayers and water channels of the stratum corneum.

Referring to FIG. 2, a schematic representation of the epidermal and dermal skin layers is shown. The outer most layer of the epidermis 10 is the stratum corneum 12. Below the stratum corneum lies the stratum lucidum 14, the stratum *granulosum* 16, the stratum *spinosum* 18, and the stratum basale 20 layers (collectively, reference numeral 22). Referring to FIG. 3, the stratum corneum comprises lipid bilayers 30 and water channels 32. The lipid bilayers 30 predominantly comprise ceramides, cholesterol, and free fatty acid (FFA) mixtures arranged in a highly matrixed head/tail configuration, represented by the head groups 32 and tail groups 34, shown schematically in FIG. 3.

Figure 4:
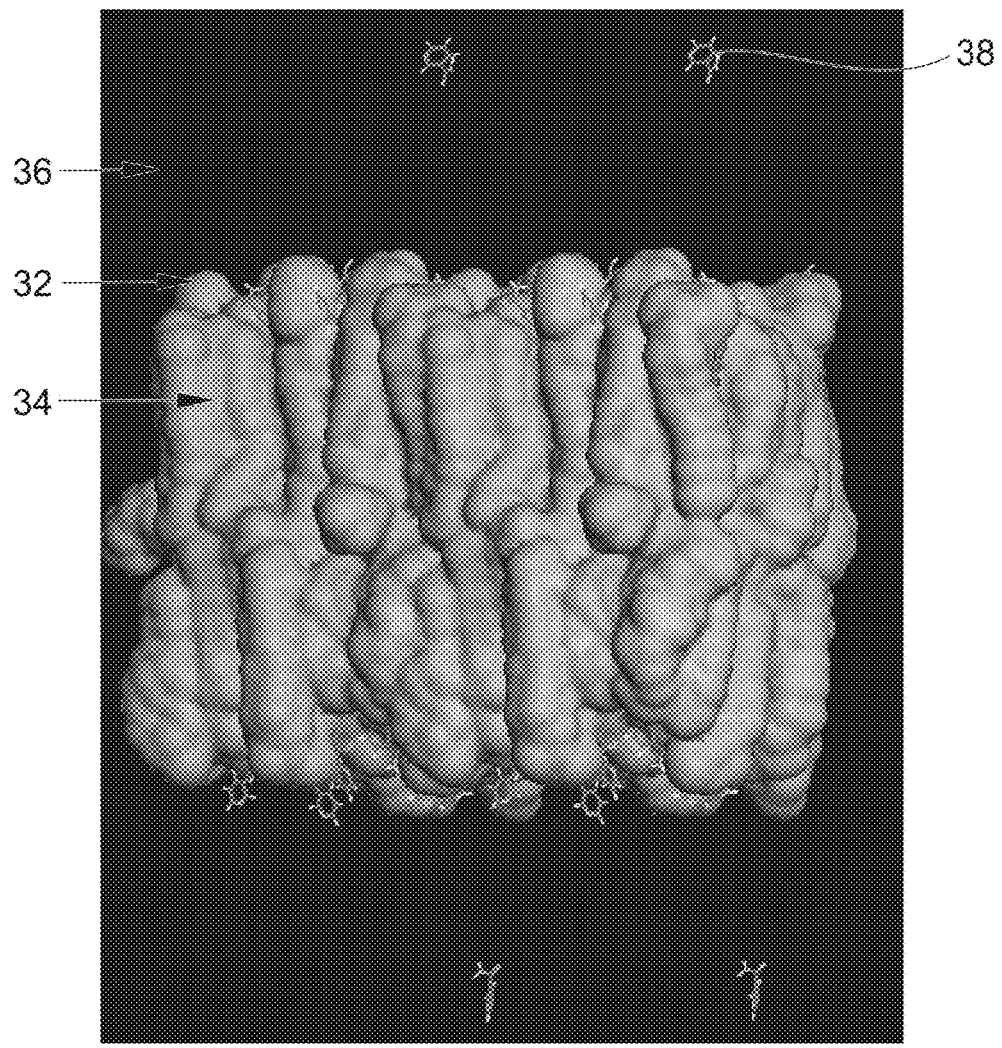
FIG. 4 is a graphic depiction from an in silico model of a lipid bilayer and water channels of the stratum corneum, wherein molecules of niacinamide are shown.
Figure 5:
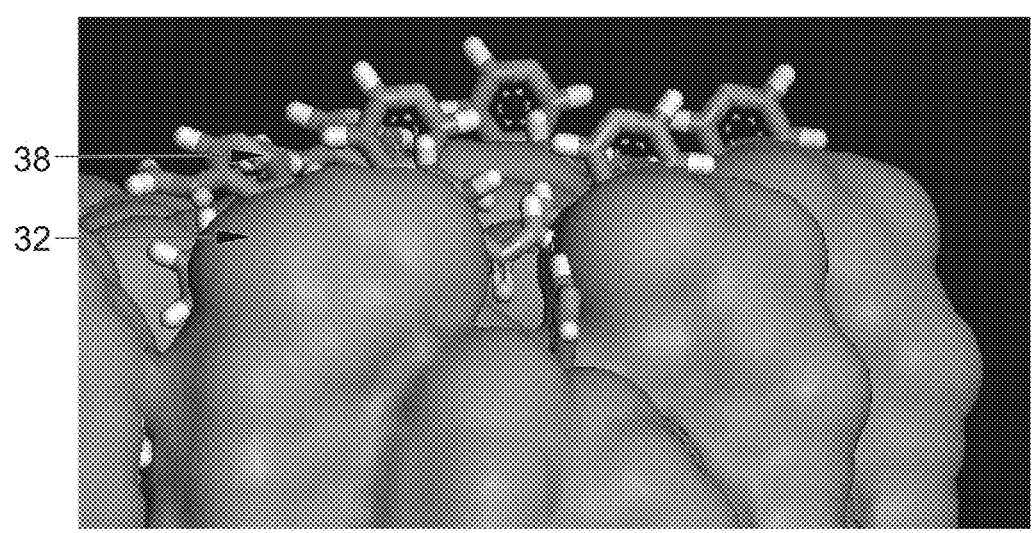
FIG. 5 is an enlargement of a portion of the lipid bilayer shown in FIG. 5, wherein niacinamide molecules are shown embedded in the head groups of the lipid bilayer.
Figure 6:
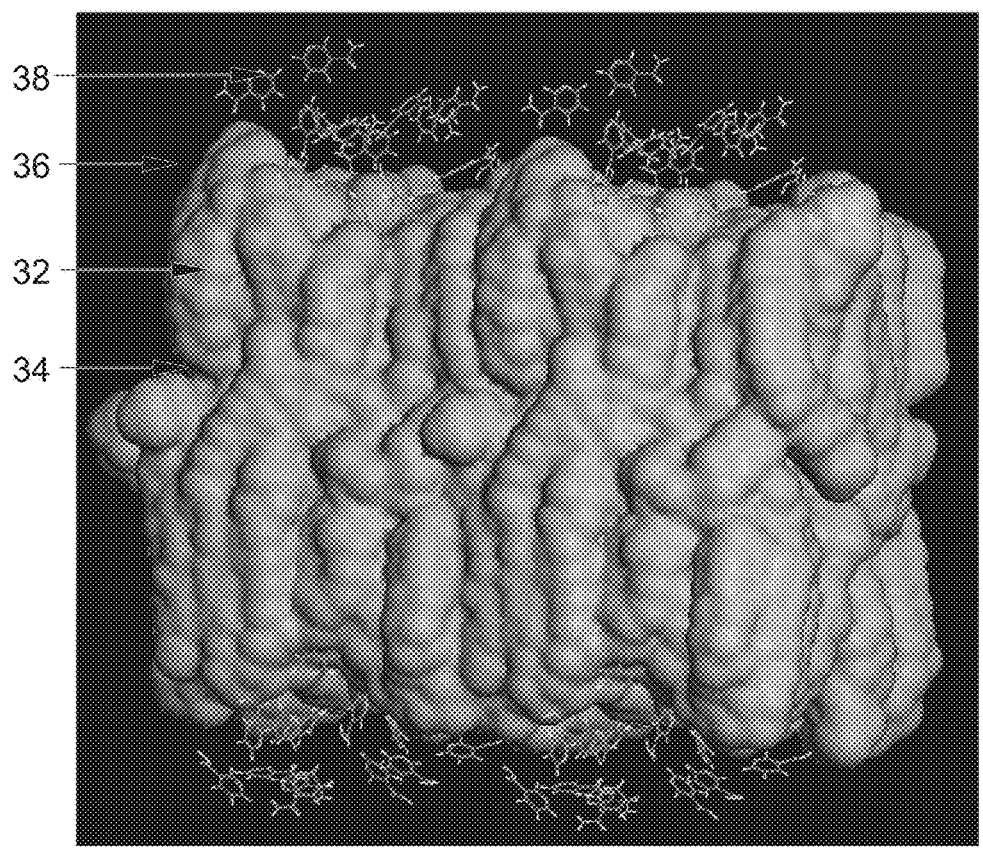
FIG. 6 graphic depiction from an in silico model of a lipid bilayer and water channels of the stratum corneum, wherein molecules of niacinamide are shown within the water channels following introduction of glycerin into the water channels.
Figure 7:
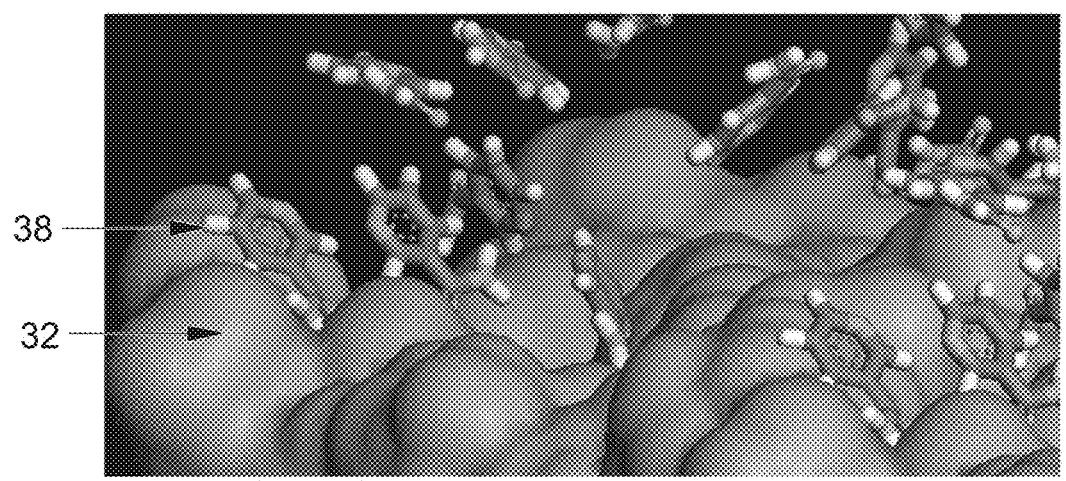
FIG. 7 is an enlargement of a portion of the lipid bilayer shown in FIG. 6.

Referring to FIGS. 4 and 5, atomistic in-silico modeling of a lipid bilayer region suggests a possible explanation for the in vitro glycerin effect previously discussed, namely the effect of decreasing niacinamide penetration into the skin when glycerin is present in a cosmetic composition. FIGS. 4 and 5 illustrate an in silico model of the lipid bilayer region of the stratum corneum, where heads groups 32 and tails groups 34 of the lipids are shown in a packed arrangement. In between the opposing head groups are the water channels 36. The in silico model suggests that niacinamide molecules 38, when only interacting with water molecules of the water channels, will distribute themselves between sitting on the head group surface of the lipid bilayer and dissolving in the water of the water channels. In comparison, FIGS. 6 and 7 illustrate the effect of glycerin on niacinamide 38 in the water channels 36. It appears that glycerin favorably binds to the hydrophilic head groups of the lipid bilayers and to itself via effective H-bonding and networking, thereby essentially "gelling" the water channel and entrapping the niacinamide molecules within the water channels to retard penetration of niacinamide through the water channels.

III. VITAMIN B COMPOUNDS, GLYCERIN, AND PENETRATION ENHANCERS

While it is has been observed, both in vitro and in silico, that glycerin may sometimes be an impediment to the penetration of niacinamide through the skin, it has been discovered that certain ingredient(s), collectively known as penetration enhancers, such as unsaturated fatty acids, e.g. undecylenoyl-L-phenylalanine, hexyldecanol (e.g. 2-hexyl-1-decanol), octyl salicylate, isopropyl lauroyl sarcosinate, oleic acid, isostearic acid may counteract this effect and, in some instances, enable glycerin to synergistically enhance rather than retard penetration of niacinamide into and through the stratum corneum.

Referring to Example 2, penetration of radio-labeled niacinamide into skin (Examples 2A and 2B used cadaver skin, Examples 2C and 2D used pig skin) was assessed over a 24 hour time period using a Franz diffusion cell system, which is a well known device in the art for measuring penetration of compounds into skin samples. Table 1 below summarizes the total percentage dose of niacinamide recovered from the combination of the epidermis, dermis, and the Franz Cell Receptor (which represents total niacinamide penetration through the skin during the test period) after application of the cosmetic compositions set forth in Examples 2A, 2B, 2C, and 2D. Six replicates were tested for each cosmetic composition. The cosmetic composition of Example 2A included 5% niacinamide (shown in the table as "N") and 7% glycerin (shown in the table as "G"). The cosmetic composition of Example 2B included 5% niacinamide, 7% glycerin and 5% hexyldecanol (shown in the table as "HD"). The cosmetic composition of Example 2C included 5% niacinamide and 5% glycerin, and the cosmetic composition of Example 2D included 5% niacinamide, 5% glycerin, and 1% octyl salicylate (shown in the table as "OS").

TABLE 1

|  | Example 2A 5% N/7% G | Example 2B 5% N/7% G/ 5% HD | Example 2C 5% N/5% G | Example 2D 5% N/5% G/ 1% OS |
|---|---|---|---|---|
| Sample #1 | 32.43 | 64.29 | 75.22 | 97.44 |
| Sample #2 | 38.04 | 91.75 | 98.26 | 94.54 |
| Sample #3 | 20.91 | 72.08 | 99.17 | 76.62 |
| Sample #4 | 29.43 | 93.78 | 76.52 | 97.63 |
| Sample #5 | 32.60 | 68.24 | 75.65 | 99.1 |
| Sample #6 | 30.64 | 46.33 | 75.56 | 89.29 |
| Avg | 30.68 | 72.74 | 83.4 | 92.44 |
| Stdv | 5.62 | 17.85 | 11.88 | 8.5 |
| P value |  | 0.002 |  | 0.16 |

Figure 8A:
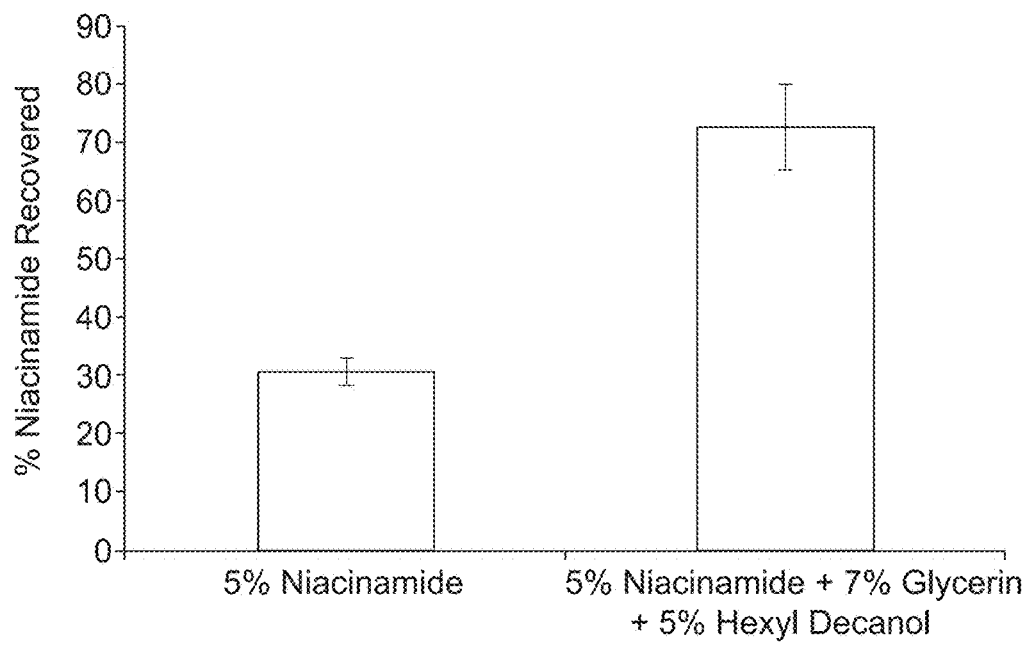
FIGS. 8A and 8B are graphs showing percentage niacinamide penetration through skin with compositions containing glycerin and different penetration enhancers.
Figure 8B:
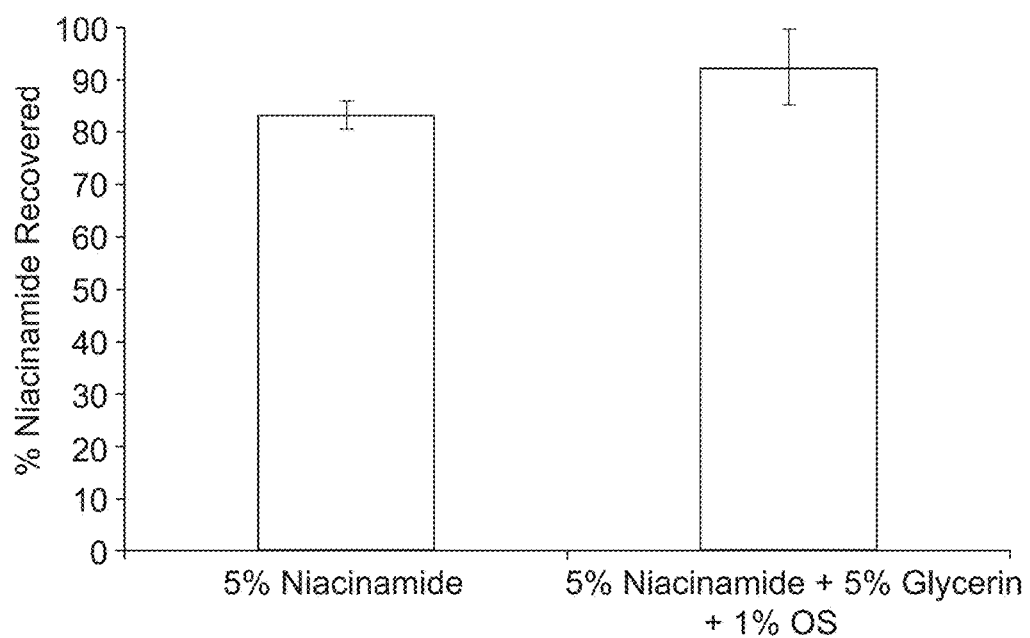

FIGS. 8A and 8B show, in graph format, the total percentage dose of niacinamide recovered from the combination of the epidermis, dermis, and the Franz Cell Receptor (which represents total niacinamide penetration through the skin during the test period) after application of the cosmetic compositions. Comparing Examples 2A and 2B (FIG. 8a), it can be seen that the addition of 5% hexyldecanol to the control composition of 5% niacinamide and 7% glycerin increased the total niacinamide penetration from 31% to 73%. Comparing Examples 2C and 2D (FIG. 7B), it can be seen that the addition of 1% octyl salicylate to the control composition of 5% niacinamide and 5% glycerin increased the total amount of skin penetration from 83% to 93%.

This data appears to support the proposition previously discussed, namely that the negative impact that glycerin can have on niacinamide penetration can be reduced or mitigated by the addition of a penetration enhancer, such as hexyldecanol or octyl salicylate.

Hexyldecanol has the following structure

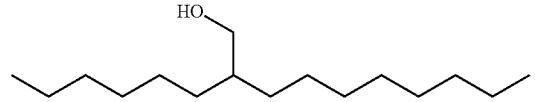 [SMILES: CCCCCCCCC(CO)CCCCCC]

Octyl salicylate has the following structure:

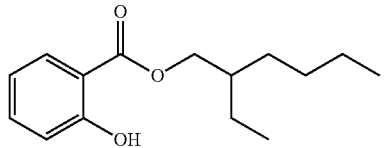 [SMILES: CCCCC(CC)COC(=O)c1ccccc1O]

Hexyldecanol and octyl salicylate are two examples of penetration enhancers that may be used. Alternatively and/or additionally, the following penetration enhancers may be used:

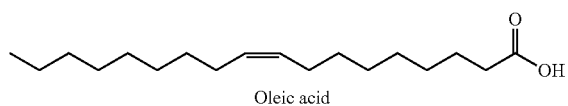
Oleic acid

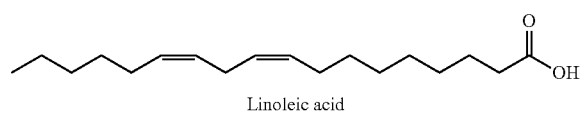
Linoleic acid

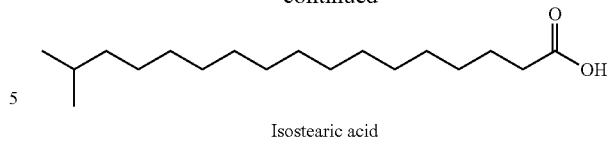
Isostearic acid

IV. VITAMIN B COMPOUNDS, GLYCERIN, PENETRATION ENHANCERS AND GLYCERYL ESTERS AND/OR GLYCERYL ETHERS

The main function of the epidermis is to act as the body's protective barrier, holding in vital water and keeping out pathogens. The epidermis itself is made of multiple layers, one of which is the stratum corneum. Within the stratum corneum is a lamellar lipid bilayer which plays an important role in maintaining the barrier properties of the skin. When the lipid bilayer is disrupted and becomes less organized, then its ability to function as a barrier is negatively impacted.

It has been found that there are materials, known herein as lipid bilayer structurants, which impact the lipid bilayer allowing for improvement of its barrier function and leading to better skin hydration. A sub-class of these lipid bilayer structurants have glyceryl head groups.

Examples of lipid bilayer structurants with a glyceryl head group include, but are not limited to:

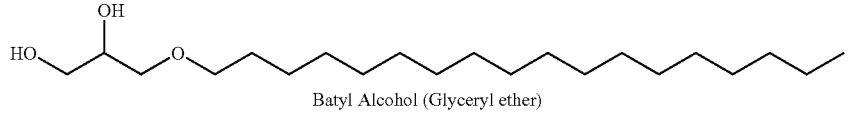
Batyl Alcohol (Glyceryl ether)

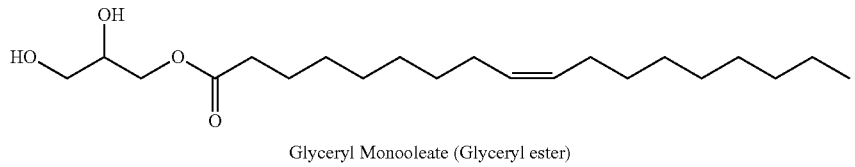
Glyceryl Monooleate (Glyceryl ester)

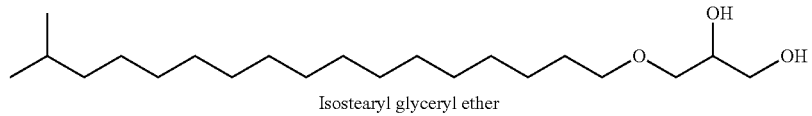
Isostearyl glyceryl ether

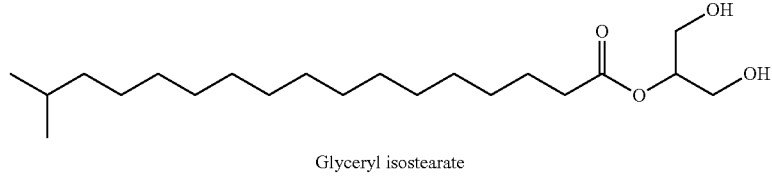
Glyceryl isostearate

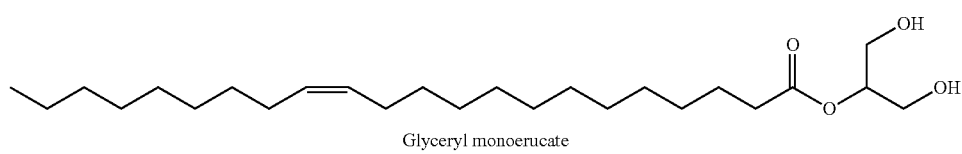
Glyceryl monoerucate

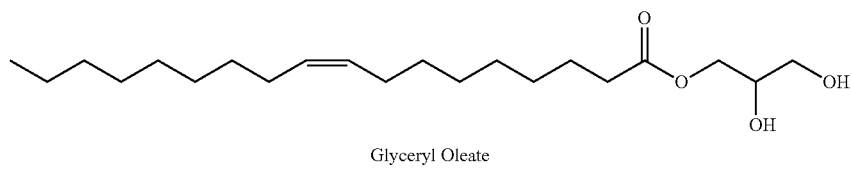
Glyceryl Oleate

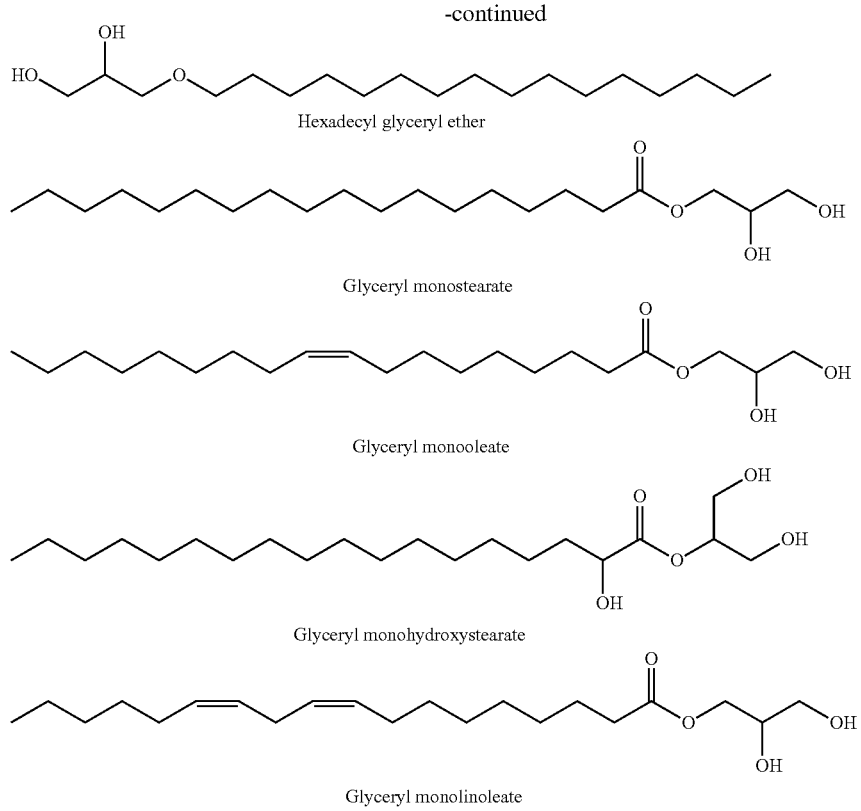

It has surprisingly been found that inclusion of a lipid bilayer structurant with a glyceryl head group in a composition containing glycerin, niacinamide and a penetration enhancer, retards movement of the skin care active through skin as a result of synergistic interactions between the lipid bilayer structurant and both the penetration enhancer and glycerin. The end result is increased overall penetration into skin of a skin care active (vs not having a penetration enhancer) and increased residency time of the skin active within layers of skin (vs use of a penetration enhancer without a lipid bilayer structurant).

Figure 9:
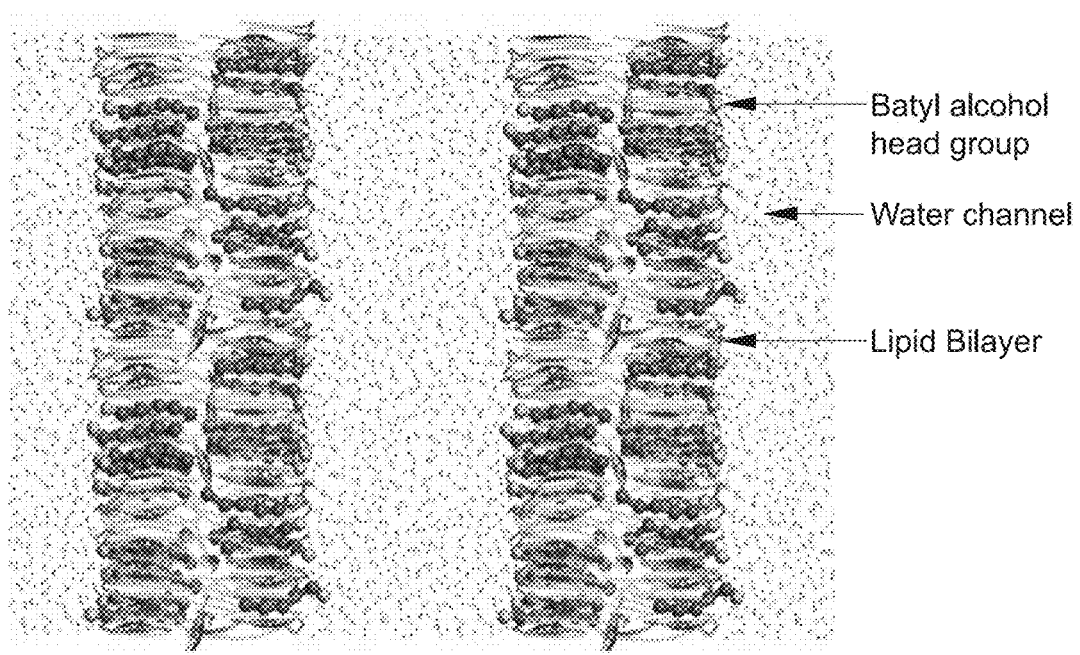
FIG. 9 is a graphic depiction from an in silico model of a lipid bilayer and water channels of the stratum corneum, showing the interaction between lipid bilayer structurants with glyceryl headgroups and the lipid bilayer.

FIG. 9 illustrates the interaction between the glyceryl head group of the lipid bilayer structurant (in this case, batyl alcohol) and glycerin using in silico modeling. It can be seen that the head group of the batyl alcohol is embedded amongst the head groups of the lipid bilayer, effectively anchoring the glycerin in the stratum corneum lipid bilayer. The backbone of the batyl alcohol molecules nests within the hydrophobic tails of the lipid bilayer. The positioning of the backbones of the batyl alcohol increases the overall integrity of the lipid bilayer while the nestled head groups increase viscosity of the surrounding water channels, thus slowing down progress of a skin care active through skin.

Figure 10:
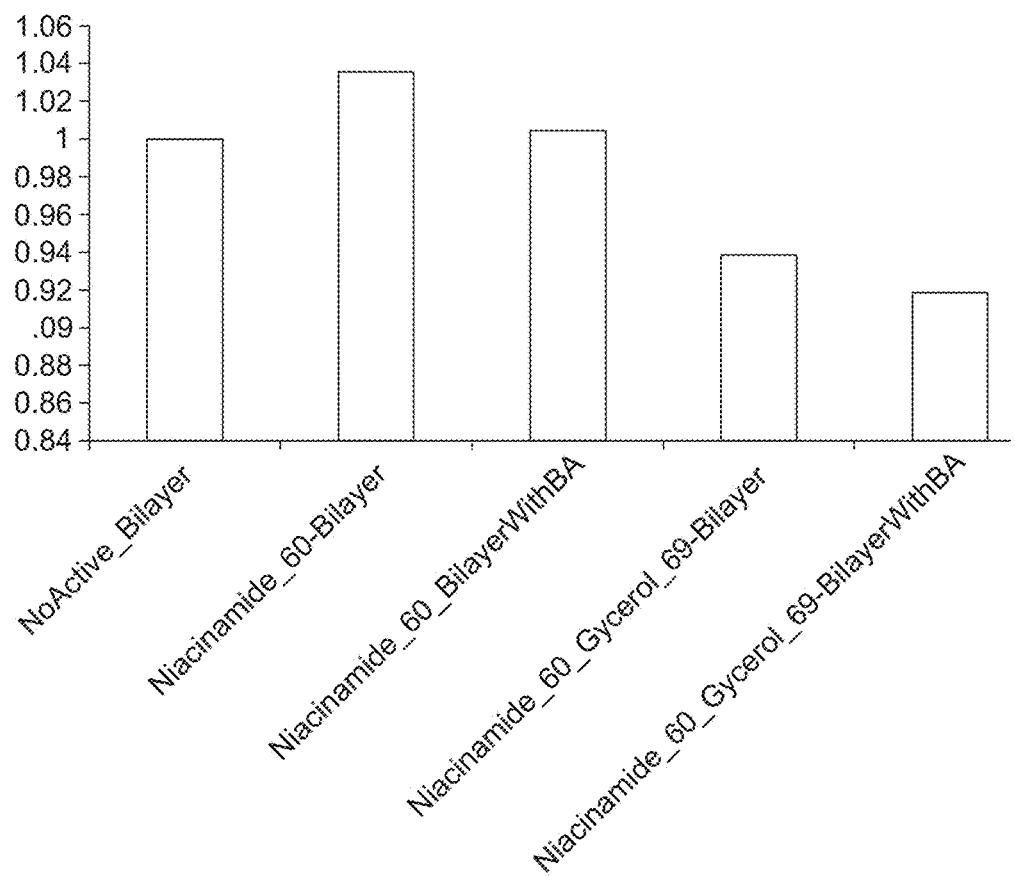
FIG. 10 is a graph showing a comparison of diffusivity of water channels in the lipid bilayer when glycerin and batyl alcohol are combined together.

FIG. 10 illustrates the effect on diffusivity of water in lipid bilayers when batyl alcohol and glycerin are added. The diffusivity of water in the lipid bilayer without inclusion of any actives, penetration enhancer or lipid bilayer structurant is normalized to "1". The diffusivity of the water increases when niacinamide is added and re-levels to approximately "1" when both niacinamide and batyl alcohol are added and reduces further when niacinamide and glycerin are added. When both glycerin and batyl alcohol are added together with niacinamide, the diffusivity of water decreases further still, proving the synergistic benefit of including combing glycerin together with a lipid bilayer structurant, such as batyl alcohol, to increase viscosity of water within the lipid bilayers, thus slowing down progress of niacinamide through the skin.

Figure 11A:
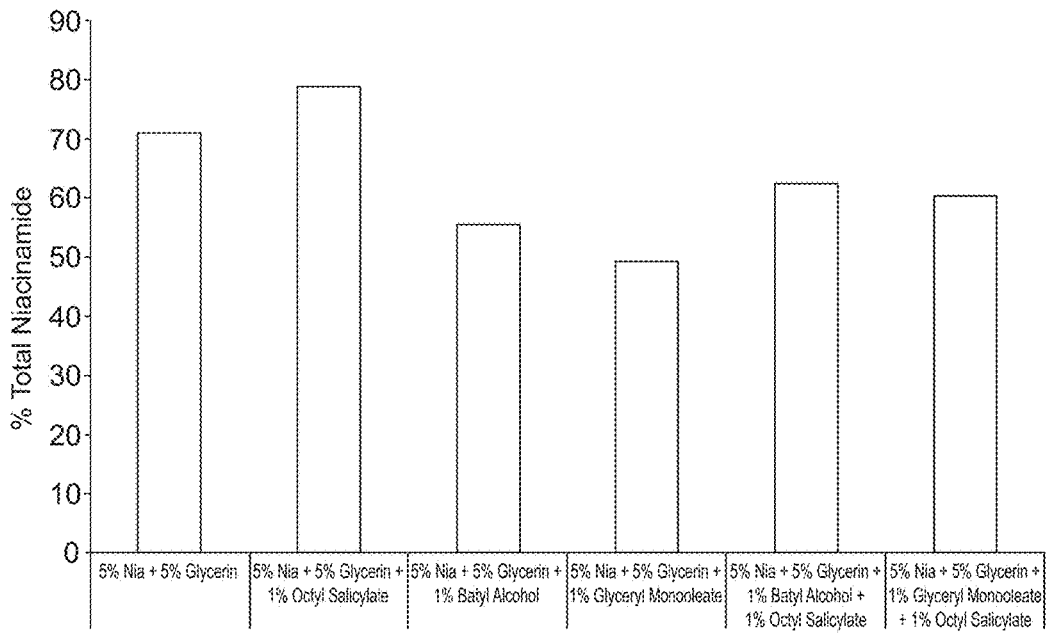
FIG. 11A is a graph showing the comparison in total skin penetration of niacinamide for compositions with and without a lipid bilayer structurant.
Figure 11B:
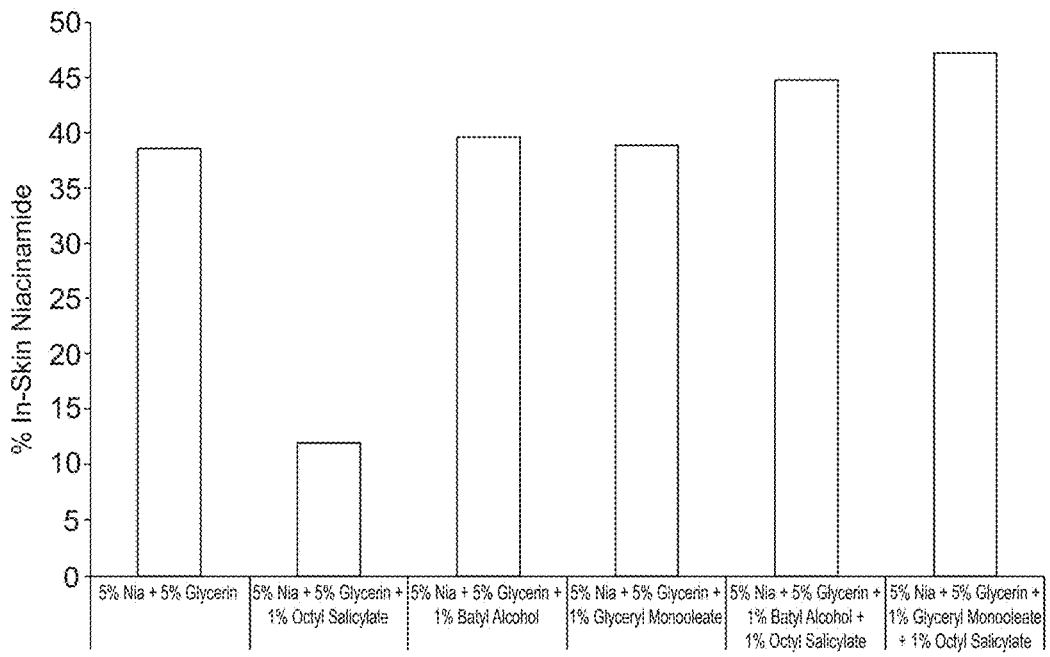
FIG. 11B is a graph showing the comparison in in-skin presence of niacinamide for compositions with and without a lipid bilayer structurant.

Referring to Example 3, penetration of radiolabeled niacinamide into cadaver skin was assessed using the same Franz Diffusion Cell system as previously discussed for Example 2. Table 2 below summarizes the total percentage dose of niacinamide recovered from the combination of the epidermis, dermis, and the Franz Cell Receptor after application of the cosmetic compositions set forth in Examples 3A, 3B, 3C, 3D, 3E and 3F. Table 3 shows the total percentage dose of niacinamide found in skin after application of the cosmetic compositions set forth in Examples 3A, 3B, 3C 3D, 3E and 3F. The results of Table 2 and Table 3 are illustrated graphically in FIGS. 11A and 11B. The cosmetic composition of Example 3A included 5% niacinamide and 5% glycerin. Example 3B included 5% niacinamide, 5% glycerin and 1% octyl salicilate (penetration enhancer). Example 3C included 5% niacinamide, 5% glycerin and 1% batyl alcohol. Example 3D included 5% niacinamide, 5% glycerin and 1% glyceryl monooleate. Example 3E included 5% niacinamide, 5% glycerin, 1% octyl salicilate and 1% batyl alcohol. Example 3F included 5% niacinamide, 5% glycerin, 1% octyl salicilate and 1% glyceryl monooleate.

TABLE 2

| % Recovery (Total) | 3A 5% Nia + 5% Glycerin | 3B 5% Nia + 5% Glycerin + 1% Octyl Salicylate | 3C 5% Nia + 5% Glycerin + 1% Batyl Alcohol | 3D 5% Nia + 5% Glycerin + 1% Glyceryl Monooleate | 3E 5% Nia + 5% Glycerin + 1% Batyl Alcohol + 1% Octyl Salicylate | 3F 5% Nia + 5% Glycerin + 1% Glyceryl Monooleate + 1% Octyl Salicylate |
|---|---|---|---|---|---|---|
| Leg 1 | 60.05 | 83.14 | 47.87 | 54.70 | 49.57 | 60.82 |
| Leg 2 | 69.58 | 80.66 | 50.70 | 48.33 | 44.60 | 51.44 |
| Leg 3 | 76.14 | 65.37 | 51.72 | 55.10 | 70.57 | 62.53 |
| Leg 4 |  | 83.30 | 55.72 | 46.32 | 67.33 | 66.14 |
| Leg 5 | 63.61 | 84.56 | 64.34 | 46.45 | 69.76 | 59.40 |
| Leg 6 | 86.42 | 76.19 | 62.28 | 45.01 | 72.95 | 61.77 |
| avg | 71.16 | 78.87 | 55.44 | 49.32 | 62.46 | 60.35 |
| std | 10.50 | 7.25 | 6.63 | 4.45 | 12.15 | 4.92 |
| sem | 4.69 | 2.96 | 2.71 | 1.82 | 4.96 | 2.01 |
| p-value vs. 3A |  | 0.18 | 0.01 | 0.001 | 0.24 | 0.05 |

TABLE 3

| % In-skin | 3A 5% Nia + 5% Glycerin | 3B 5% Nia + 5% Glycerin + 1% Octyl Salicylate | 3C 5% Nia + 5% Glycerin + 1% Batyl Alcohol | 3D 5% Nia + 5% Glycerin + 1% Glyceryl Monooleate | 3E 5% Nia + 5% Glycerin + 1% Batyl Alcohol + 1% Octyl Salicylate | 3F 5% Nia + 5% Glycerin + 1% Glyceryl Monooleate + 1% Octyl Salicylate |
|---|---|---|---|---|---|---|
| Leg 1 | 29.36 | 2.98 | 39.06 | 51.96 | 34.01 | 53.76 |
| Leg 2 | 48.91 | 3.14 | 46.86 | 43.83 | 37.52 | 45.03 |
| Leg 3 | 32.07 | 47.75 | 40.73 | 46.14 | 51.56 | 55.69 |
| Leg 4 |  | 4.12 | 39.82 | 33.00 | 49.29 | 55.83 |
| Leg 5 | 29.55 | 2.94 | 36.35 | 38.07 | 47.60 | 37.80 |
| Leg 6 | 53.60 | 10.92 | 34.74 | 20.33 | 48.56 | 35.35 |
| avg | 38.70 | 11.97 | 39.59 | 38.89 | 44.76 | 47.24 |
| std | 11.63 | 17.79 | 4.21 | 11.20 | 7.17 | 9.20 |
| sem | 5.20 | 7.26 | 1.72 | 4.57 | 2.93 | 3.76 |
| p-value vs. 3A |  | 0.02 | 0.86 | 0.98 | 0.32 | 0.21 |

Comparing examples 3A and 3B, the cosmetic composition of Example 3B shows increased total skin penetration of Niacinamide vs. Example 3A, confirming that introduction of a penetration enhancer into the composition mitigates historical problems associated with the use of glycerin with skin care actives. However, the amount of in-skin Niacinamide in Example 3B is significantly reduced vs Example 3A. In this respect, it is known that the penetration enhancer (octyl salicylate) disrupts the lipid bilayer to allow penetration of the skin care active into skin. However, this disruption of the lipid bilayer results in a significant proportion of the skin care active passing directly through skin. Comparing Examples 3C and 3D with 3A, the cosmetic composition of Examples 3C and 3D show decreased total skin penetration vs Example A, and the same or increased in skin penetration vs Example 3A. Comparing Examples 3E and 3F with Example 3A, the cosmetic compositions of Examples 3E and 3F show a slight decrease in total skin penetration of niacinamide, but a significant increase in in-skin penetration. Thus, it can be seen that an average of 44% (Example 3E) and 47% (Example 3F) of the total amount of niacinamide that enters the skin remains within the skin's layers for the duration of the test.

Surprisingly, this data suggests that it is possible to achieve a higher overall percentage of penetration of niacinamide in skin in the presence of glycerin, a penetration enhancer and a lipid-bilayer structurant with a glyceryl head, compared with combining glycerin and niacinamide with either just a penetration enhancer or a lipid bilayer structurant with a glyceryl head.

In some examples, the cosmetic compositions described herein may have a percentage concentration by weight of glycerin of between about 1%, 2%, 3%, 4% or 5% and 10%, 15%, 20%, 15% or 30%.

In some examples, the cosmetic compositions described herein may have a percentage concentration by weight of penetration enhancer between about 0.01%, 0.1%, 0.2%, 0.5% or 1% and 4%, 5%, 6.5%, 8% or 10%.

In some examples, the cosmetic compositions described herein may have a percentage concentration by weight of lipid bilayer structurant between about 0.05%, 0.1%, 0.2%, 0.3%, 0.4%, 0.5% or 0.6% and 1%, 1.25%, 1.5%, 2%, 2.5% or 3%.

In some examples, the lipid bilayer structurant with glyceryl head group has a tail length of greater than C14, C15 or C16. In preferred embodiments, the lipid bilayer structurant with glyceryl head group has a tail length of less than C20, C19 or C18. In this respect, tails of the lipid bilayer typically have a length of between approximately C16 to C18, so having a lipid bilayer structurant with a corresponding tail length re-enforces the integrity of the bilayer.

V. OTHER INGREDIENTS

In addition to the previously described ingredients, the cosmetic compositions described herein may also comprise one or more optional ingredients. For example, the cosmetic composition may comprise from about 1% to about 95% by weight of water. The cosmetic composition may comprise from about 1% to about 95% by weight of one or more oils. The cosmetic composition may comprise from about 0.1%, 0.5%, 1%, 2%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, 5%, or 3% of the one or more oils. Oils may be used to solubilize, disperse, or carry materials that are not suitable for water or water soluble solvents. Suitable oils include silicones, hydrocarbons, esters, amides, ethers, and mixtures thereof. Oils may be fluid at room temperature. The oils may be volatile or nonvolatile. "Non-volatile" means a material that exhibits a vapor pressure of no more than about 0.2 mm of mercury at 25° C. at one atmosphere and/or a material that has a boiling point at one atmosphere of at least about 300° C. "Volatile" means that the material exhibits a vapor pressure of at least about 0.2 mm. of mercury at 20° C. Volatile oils may be used to provide a lighter feel when a heavy, greasy film is undesirable. When the cosmetic composition is in the form of an emulsion, oils are carriers typically associated with the oil phase. The cosmetic composition can be in the form of a water-in-oil emulsion, an oil-in-water emulsion, or a water-in-silicone emulsion.

Suitable oils include volatile oils. In certain embodiments, the volatile oils may have a viscosity ranging from about 0.5 to 5 centistokes at 25° C. Volatile oils may be used to promote more rapid drying of the cosmetic composition after it is applied to skin. Nonvolatile oils are also suitable for use in the cosmetic composition. Nonvolatile oils are often used for emolliency and protective properties.

Suitable silicone oils include polysiloxanes. Polylsiloxanes may have a viscosity of from about 0.5 to about 1,000,000 centistokes at 25° C. Such polysiloxanes can be represented by the general chemical formula:

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular weight. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

wherein R and R are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as 2502 Cosmetic Fluid from Dow Corning or as Abil Wax 9801 or 9814 from Evonik Goldschmidt GmbH.

Cyclic silicones are one type of silicone oil that may be used in the cosmetic composition. Such silicones have the general formula:

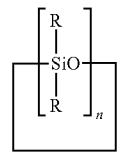

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Suitable hydrocarbon oils include straight, branched, or cyclic alkanes and alkenes. The chain length may be selected based on desired functional characteristics such as volatility. Suitable volatile hydrocarbons may have between 5-20 carbon atoms or, alternately, between 8-16 carbon atoms.

Other suitable oils include esters. The suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, C12-15 alkyl benzoate, diisopropyl adipate, dibutyl adipate, and oleyl adipate. Other suitable esters are further described in the Personal Care Product Council's *International Cosmetic Ingredient Dictionary and Handbook*, Thirteenth Edition, 2010, under the functional category of "Esters." Other esters suitable for use in the cosmetic composition include those known as polyhydric alcohol esters and glycerides.

Other suitable oils include amides. Amides include compounds having an amide functional group while being liquid at 25° C. and insoluble in water. Suitable amides include N-acetyl-N-butylaminopropionate, isopropyl N-lauroylsarcosinate, and N,N-diethyltoluamide. Other suitable amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

The cosmetic composition may comprise an emulsifier. An emulsifier is particularly suitable when the cosmetic composition is in the form of an emulsion or if immiscible materials are being combined. The cosmetic composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic, or cationic. Non-limiting examples of emulsifiers are disclosed in U.S. Pat. Nos. 3,755,560, 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifiers include the following classes of ethers and esters: ethers of polyglycols and of fatty alcohols, esters of polyglycols and of fatty acids, ethers of polyglycols and of fatty alcohols which are glycosylated, esters of polyglycols and of fatty acids which are glycosylated, ethers of $C_{12-30}$ alcohols and of glycerol or of polyglycerol, esters of $C_{12-30}$ fatty acids and of glycerol or of polyglycerol, ethers of oxyalkylene-modified $C_{12-30}$ alcohols and of glycerol or polyglycerol, ethers of $C_{12-30}$ fatty alcohols comprising and of sucrose or of glucose, esters of sucrose and of $C_{12-30}$ fatty acids, esters of pentaerythritol and of $C_{12-30}$ fatty acids, esters of sorbitol and/or of sorbitan and of $C_{12-30}$ fatty acids, ethers of sorbitol and/or of sorbitan and of alkoxylated sorbitan, ethers of polyglycols and of cholesterol, esters of $C_{12-30}$ fatty acids and of alkoxylated ethers of sorbitol and/or sorbitan, and combinations thereof.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu.

Emulsifiers also include emulsifying silicone elastomers. Suitable emulsifying silicone elastomers may include at least one polyalkyl ether or polyglycerolated unit. Polyoxyalylenated emulsifying silicone elastomers that may be used include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011. Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Structuring agents may be used to increase viscosity, thicken, solidify, or provide solid or crystalline structure to the cosmetic composition. Structuring agents are typically grouped based on solubility, dispersibility, or phase compatibility. Examples of aqueous or water structuring agents include polymeric agents, natural or synthetic gums, polysaccharides, and the like. For example, the cosmetic composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the cosmetic composition, of one or more structuring agents.

Polysaccharides and gums may be suitable aqueous phase thickening agents. Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes, Suitable silicone elastomers may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersions include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crossoplymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-41, KSG-42, KSG-43, and KSG-44, wherein the elastomer is dispersed in solvents including mineral oil, isodocane, triethylhexanoin, or squalene, respectively. Other suitable silicone elastomers may have polyglycerine substitutions such as lauryl dimethicone/polyglycerin-3 crosspolymers supplied by Shin Etsu under the tradenames KSG-810, KSG-820, KSG-830, and KSG-840, wherein the elastomer is dispersed in solvents including mineral oil, isodocane, triethylhexanoin, or squalene, respectively. Other suitable silicone elastomers may have polyglycol substitutions such as PEG-15/lauryl dimethiconecrosspolymers supplied by Shin Etsu under the tradenames KSG-310, KSG-320, KSG-330, and KSG-340, wherein the elastomer is dispersed in solvents including mineral oil, isodocane, triethylhexanoin, or squalene, respectively. Other suitable silicone elastomers having polyglycol substitutions include Shin Etsu's KSG-210, a dimethicone/PEG-10/15 crosspolymer in dimethicone.

Silicone gums are another oil phase structuring agent. The silicone gum typically has a viscosity ranging from about 500,000 to 100 million cst at 25° C., from about 600,000 to 20 million, from about 600,000 to 12 million cst. Suitable silicone gums include those sold by Wacker-Belsil under the trade names CM3092, Wacker-Belsil 1000, or Wacker-Belsil DM 3096. A particularly suitable silicone gum is as dimethiconol, available from Dow Corning Corporation under the trade name 1-1254 Fluid, 2-9023 Fluid, and 2-9026 Fluid. Dimethiconol is often sold as a mixture with a volatile or nonvolatile silicone such as Dow Corning 1401 Fluid, 1403 Fluid, and 1501 Fluid.

Another type of oily phase structuring agent includes silicone waxes. Silicone waxes may be referred to as alkyl silicone waxes and can be semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable viscosity increasing agents include polyamides and polysilicone-polyamide copolymers. Suitable polysilicone-polyamide copolymers are disclosed in U.S. Patent Application Publication No. 2004/0170586.

Other oil phase structuring agents may be one or more natural or synthetic waxes such as animal, vegetable, or mineral waxes. Suitable silicone waxes are disclosed in U.S. Pat. Nos. 5,413,781 and 5,725,845, and further include alkylmethyl polysiloxanes, C10-C60 alkyl dimethicones, and mixtures thereof.

Other structuring agents include natural or synthetic montmorillonite minerals, silicas, silicates, silica silylate, and alkali metal or alkaline earth metal derivatives thereof.

The cosmetic compositions may optionally contain a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010. Suitable UV actives include those defined or proposed by regulatory agencies in the US (e.g., 21 CFR part 352, 68 Federal Register 41386, 70 Federal Register 72449, or 71 Federal Register 42405), Europe (Regulation No 1223/2009 of the EU Parliament; Annex VI), Japan, China, Australia, New Zealand, or Canada. For example, the cosmetic composition may comprise from about 0.01% to about 20%, by weight of the cosmetic composition, of a UV active. The cosmetic composition may also comprise a sufficient amout of UV active to yield a Sun Protection Factor of at least about 15, 30 45, or 50. SPF testing is conventional and well understood in the art. A suitable SPF test is prescribed in 21 C.F.R. 352, Subpart D.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone) (commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzonphenone-3 (i.e. oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-tri-methylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures thereof.

Particularly suitable UV actives are 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

The cosmetic compositions may be generally prepared by conventional methods such as those known in the art of making cosmetic compositions. Such methods typically involve mixing of ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The cosmetic compositions are preferably prepared such as to optimize stability (physical stability, chemical stability, photostability, etc.) and/or delivery of active materials. The cosmetic composition may be provided in a package sized to store a sufficient amount of the cosmetic composition for a treatment period. The size, shape, and design of the package may vary widely. Certain package examples are described in U.S. Pat. Nos. 570,707; 391,162; 516,436; 535,191; 542,660; 547,193; 547,661; 558,591; 563,221; 2009/0017080; 2007/0205226; and 2007/0040306.

VI. METHODS OF USE

The cosmetic compositions disclosed herein may be applied to one or more skin surfaces as part of a user's daily routine. Additionally or alternatively, the cosmetic compositions herein may be used on an "as needed" basis. For example, the cosmetic composition may be applied to a facial skin care surface in need of treatment by the cosmetic composition. The facial skin surface may include one or more of the cheek, forehead, and peri-orbital areas of the face. In some examples, one or more of these skin surfaces may be identified as needing treatment and one or more of these skins surfaces may be treated with the cosmetic composition. For example, the cosmetic composition can also be applied to the facial skin surface at least once per day, twice per day, or three times per day for a period of 7, 14, 21, or 28 days or more. In another example, the cosmetic composition may be applied to a different skin surface or applied to facial skin and one or more different skin surfaces.

VII. EXAMPLES

The following examples are given solely for the purpose of illustration and are not to be construed as limiting the invention, as many variations thereof are possible.

Example 1—Niacinamide/Glycerin Measurements

In vitro skin penetration studies were conducted to characterize the impact of glycerin upon in vitro skin penetration of radiolabeled niacinamide in several cosmetic compositions. The kinetics of in vitro radiolabeled niacinamide skin penetration were determined at a fixed glycerin concentration, and the impact of glycerin and niacinamide product concentrations upon the skin penetration of radiolabeled niacinamide and glycerin over six hours were measured. Table 5 provides a general description of the four cosmetic composition types that were tested.

TABLE 4

General descriptions of the chassis used in the in vitro skin permeation experiments

| Chassis (wt %) | Composition #1 | Composition #2 | Composition #3 | Composition #4 |
|---|---|---|---|---|
| Type | O/W Emulsion | W/Si Emulsion | W/Si Emulsion | Water Gel |
| Water | 72.3 | 65.7 | 48.8 | ~78 |
| Polyols |  | 2.0 | 3.0 | 3.2 |
| Silicone | 2.0 | 12.8 | 34.7 | 1.5 |
| Oil | 5.0 |  |  | 1.5 |
| Emulsifiers | Nonionic Surfactant Acrylic Copolymers Fatty Alcohols | Silicone Elastomers | Silicone Elastomers | Nonionic Acrylic Copolymers |

Split thickness cadaver skin was obtained from AlloSource (Englewood, Colo.). Tritiated water was from PerkinElmer (Boston, Mass.) while $^{14}C$ niacinamide was obtained from American Radiochemicals (St. Louis, Mo.). For all studies, split-thickness human cadaver skin was maintained at −70° C. until thawed at ambient conditions, rinsed with distilled water, cut into appropriately sized sections, and mounted in standard Franz-type diffusion cells (0.79 cm$^2$) which were placed in heating/stirring blocks thermostatted to maintain a skin surface temperature of about 34° C. The receptors [~5 mL] were filled with a solution of 1% polysorbate 20 (VWR International, West Chester, Pa.) in Dulbecco's Phosphate Buffered Saline [PBS] (Sigma-Aldrich, Inc., St. Louis, Mo.) with agitation provided by magnetic stir bars, and the skin allowed to equilibrate for at least two hours.

Six cells were randomized to each treatment in a given study based upon $^3H_2O$ flux through the mounted skin. 150 μL $^3H_2O$ were applied to the mounted cadaver skin for five minutes and any non-absorbed liquid subsequently removed with a cotton swab. After a minimum of one hour to achieve equilibrium, the receptor contents were collected. Liquid scintillation cocktail, LCS, (14 mL) was added to the contents of each receptor and also to triplicate 150 μL aliquots of $^3H_2O$. The LSC solutions and appropriate blanks were assayed for total radiolabel by liquid scintillation counting for one minute using a pre-set quench curve. Blank corrected DPM (disintegrations per minute) in each receptor was converted to μL $^3H_2O$ using the mean of the blank corrected DPM of the 150 μL aliquots of $^3H_2O$, and water flux for each cell was calculated as the quotient of the $^3H_2O$ volume detected in the receptor and the available skin surface area. Fresh receptor fluid was then added to the receptor portions of the Franz cells and the cells allowed to further equilibrate overnight.

Following the overnight equilibration period, the receptor compartments were filled with fresh media. Except as noted below, approximately 5 μL of product with radiotracer were applied to the individual cells using a positive displacement pipette. The receptor solution was collected and replaced at 2 and 4 hr with a final collection at 6 hr. At the end of the test time (s), each skin sample was wiped two times with Whatman filter paper soaked with PBS containing 1% polysorbate 20 and once with filter paper soaked with 70%/30% ethanol/distilled water to remove unabsorbed (residual) product. The epidermis (including stratum corneum) was separated from the residual dermis by dissection.

Disintegrations-per-minute (DPM) obtained for the various components of each cell (all receptor collections, filter paper wipes, epidermis, and dermis) were blank corrected and summed to obtain a total recovered radiolabel value for a given cell. This value was then compared with the specific radiolabel activity of the product (DPM/theoretical dose) to estimate the percent recovery of the theoretical dose.

The blank corrected DPM of each compartment were then normalized to the total recovered radiolabel value to obtain a "percent recovered radiolabel" parameter for each component. This compensates for variations in the amount of product dosed due to its viscosity and improves study precision.

Cumulative receptor amounts were calculated as the sums of the various receptor collections to a given time point. A total skin value was calculated as the sum of the epidermis and dermis fractions, and a total permeated value calculated as the sum of total skin and total cumulative receptor.

For those studies which incorporated test products with varying concentrations of the permeant being investigated (e.g. niacinamide), the percent recovered values were subsequently converted to "fraction radiolabel recovered" by dividing by 100, and then to amount (μg-equivalents (μg-eq)

permeant by multiplying by the target dose (5 mg) and fraction permeant in the test product.

The data from this series of studies, summarized in FIG. 1, suggests that the addition of glycerin decreases niacinamide skin penetration and that increasing the glycerin concentration further decreases niacinamide skin penetration from a variety of cosmetic compositions.

Example 2—Niacinamide/Glycerin/Hexyldecanol, Niacinamide/Glycerin/Octyl Salicylate Measurements The cosmetic compositions set forth in Table 5 were prepared.

TABLE 5

| Component (wt %) | 2A | 2B | 3A | 3B |
|---|---|---|---|---|
| Water | QS | QS | QS | QS |
| Polymer | 0.4 | 0.4 | 1 | 1 |
| Glycerin | 0 | 7 | 5 | 5 |
| Niacinamide | 5 | 5 | 5 | 5 |
| Triethanolamine | 0.5 | 0.5 | 0 | 0 |
| Polyoxyethylene (20) sorbitan monolaurate | 0 | 0 | 0.5 | 0.5 |
| 2-Hexyl-1-decanol | 0 | 5 | 0 | 0 |
| DMDM Hydantoin Iodopropynyl Butylcarbamate | 0.3 | 0.3 | 0 | 0 |
| Octyl Salicylate | 0 | 0 | 0 | 1 |
| 1,3Butylene Glycol | 0 | 0 | 2 | 2 |
| Pentylene Glycol | 0 | 0 | 3 | 3 |
| Hexylene Glycol | 0 | 0 | 0.75 | 0.75 |
| Benzyl Alcohol | 0 | 0 | 0.2 | 0.2 |
| Phenoxyethanol | 0 | 0 | 0.25 | 0.25 |
| Bisabolol | 0 | 0 | 0.1 | 0.1 |
| Amino Methyl Propanol | 0 | 0 | 0.15 | 0.15 |
| Sodium Benzoate | 0 | 0 | 0.15 | 0.15 |
| EDTA-2NA | 0 | 0 | 0.1 | 0.1 |

Next, skin samples (cadaver or pig skin) were mounted in standard Franz-type diffusion cells (0.79 cm$^2$ surface area) maintained at about 37° C. Six replicates for each compositional leg were prepared. The receptor compartments were filled with 5 mL phosphate buffered saline (PBS—pH 7.4) that included 1% polysorbate-20 and 0.02% sodium azide, and the skin allowed to equilibrate for two hours. The cells were randomized to treatment group based upon $^3$H$_2$O flux through the mounted skin (150 µL of $^3$H20 applied for five minutes, removed and followed by collection of receptor fluid after 60 minutes). Diffusion cells were randomized by ranking each cell according to water flux and distributing cells across treatment legs such that each group included cells across the range of observed water flux. Each treatment group typically had 6 replicates.

Aliquots of the test products/formulations set forth in Table 4 were spiked with $^{14}$C-niacinamide with approximately 3 µCi per 300 mg product aliquot, mixed and assayed for total radioactivity in triplicate using Ultima Gold (available from Perkin-Elmer) liquid scintillation cocktail (LSC) and liquid scintillation counting (Tri-Carb 2500 TR Liquid Scintillation Analyzer, PerkinElmer, Boston, Mass.). The skin samples were topically dosed with 5 µL of the radiolabeled niacinamide composition using a positive displacement pipette. The cosmetic composition was gently spread over the surface of the skin samples (0.79 cm$^2$) using the pipet tip. The receptor solution was collected and replaced at 6 hours following application with a final collection at 24 hrs. After the final receptor collection, each skin sample was wiped two times with Whatman filter paper soaked with PBS/Tween 20 and once with 70%/30% ethanol/water to remove unabsorbed (residual) product. The epidermis was separated from the residual dermis by dissection. The skin sections were dissolved in 0.50-1.25 mL Soluene-350 (Perkin Elmer, Boston, Mass.) at 60° C. overnight, and all receptor collections, filter paper wipes, and solubilized tissue sections were counted using liquid scintillation counting. Disintegrations-per-minute (DPM) for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total recovered percentage value was the sum of the epidermis (including stratum corneum) and dermis values, and the total permeated value the sum of total skin and cumulative receptor values. Table 1, summarizes the total percentage values of radiolabeled niacinamide recovered.

Example 3—Niacinamide/Glycerin/Glyceryl Ether/Ester/Octyl Salicylate Measurements The cosmetic compositions set forth in Table 6 were prepared in the same manner as previously described with respect to Example 2.

TABLE 6

| Component (wt %) | 3A 5% Nia + 5% Gly | 3B % 5 Nia + 5% Gly + 1% OS | 3C 5% Nia + 5% Gly + 1% Batyl OH | 3D 5% Nia + 5% Gly + 1% GMO + | 3E 5% Nia + 5% Gly + 1% Batyl OH + 1% OS | 3F 5% Nia + 5% Gly + 1% GMO + 1% OS |
|---|---|---|---|---|---|---|
| Niacinamide | 5 | 5 | 5 | 5 | 5 | 5 |
| Ultrez 20 | 0.2 | 0.2 | 0.2 | 0.2 | 0.2 | 0.2 |
| Amino Methyl Propanol | 0.15 | 0.15 | 0.15 | 0.15 | 0.15 | 0.15 |
| Pemulen TR-2 | 0.2 | 0.2 | 0.2 | 0.2 | 0.2 | 0.2 |
| Sodium Benzoate | 0.15 | 0.15 | 0.15 | 0.15 | 0.15 | 0.15 |
| EDTA-2NA | 0.1 | 0.1 | 0.1 | 0.1 | 0.1 | 0.1 |
| Sepigel 305 | 0.6 | 0.6 | 0.6 | 0.6 | 0.6 | 0.6 |
| Tween 20 | 0.5 | 0.5 | 0.5 | 0.5 | 0.5 | 0.5 |
| Glycerin | 5 | 5 | 5 | 5 | 5 | 5 |
| 1,3Butylene Glycol | 2 | 2 | 2 | 2 | 2 | 2 |

TABLE 6-continued

| Component (wt %) | 3A 5% Nia + 5% Gly | 3B % 5 Nia + 5% Gly + 1% OS | 3C 5% Nia + 5% Gly + 1% Batyl OH | 3D 5% Nia + 5% Gly + 1% GMO + | 3E 5% Nia + 5% Gly + 1% Batyl OH + 1% OS | 3F 5% Nia + 5% Gly + 1% GMO + 1% OS |
|---|---|---|---|---|---|---|
| Pentylene Glycol | 3 | 3 | 3 | 3 | 3 | 3 |
| Hexylene Glycol | 0.75 | 0.75 | 0.75 | 0.75 | 0.75 | 0.75 |
| Benzyl Alcohol | 0.2 | 0.2 | 0.2 | 0.2 | 0.2 | 0.2 |
| Phenoxyethanol | 0.25 | 0.25 | 0.25 | 0.25 | 0.25 | 0.25 |
| Batyl Alcohol | 0 | 0 | 1 | 0 | 1 | 0 |
| GMO | 0 | 0 | 0 | 1 | 0 | 1 |
| Bisabolol | 0.1 | 0.1 | 0.1 | 0.1 | 0.1 | 0.1 |
| Octyl Salicylate | 0 | 1 | 0 | 0 | 1 | 1 |

Using generally the same test procedures as set forth in Example 2, DPM for each compartment of each cell were blank corrected and summed to obtain a total recovered radiolabel value for a given cell. The DPM of each compartment were then normalized to the total recovered radiolabel value to obtain a "percent recovered radiolabel" parameter for each compartment (individual receptor collections, epidermis, dermis, and wipes for mass balance). Cumulative receptor values to each collection time point were calculated as the sum of the individual collections to that time point, with the total receptor value as the sum of all individual collections. The total percentage recovered value was the sum of the epidermis (including stratum corneum) and dermis values, and the total permeated value the sum of total skin and cumulative receptor values. Tables 2 and 3 summarize the total and In-skin percentage value of radiolabeled Niacinamide recovered for examples 3A-3F.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition that is suitable for topical application and provides enhanced penetration of niacinamide into skin, the cosmetic composition comprising:
   i) about 1% to about 30% glycerin;
   ii) about 0.05% to about 3% of a lipid bilayer structurant comprising batyl alcohol;
   iii) about 0.01% to about 10% of a penetration enhancer selected from N-undecylenoyl-L-phenylalanine, 2-hexyldecanol, octyl salicylate, isopropyl lauroyl sarcosinate, oleic acid, Isostearic acid, linoleic acid, linolenic acid, and combinations thereof; and
   iv) about 1% to about 10% niacinamide, wherein the composition provides enhanced penetration of niacinamide in an in vitro skin penetration assay as compared to an identical composition that does not include at least one of the lipid bilayer structurant and the penetration enhancer.

2. The cosmetic composition of claim 1, wherein the penetration enhancer is octyl salicylate.

3. A method of using the cosmetic composition of claim 1, comprising applying the cosmetic composition of claim 1 to a facial skin surface in need of treatment, wherein the cosmetic composition of claim 1 provides enhanced penetration of niacinamide into skin.

4. A method of increasing the percentage of niacinamide deposited in skin, the method comprising topically applying the cosmetic composition of claim 1 to skin, wherein the cosmetic composition of claim 1 increases the percentage of niacinamide deposited in the skin.

* * * * *

UNITED STATES PATENT AND TRADEMARK OFFICE
CERTIFICATE OF CORRECTION

PATENT NO. : 10,549,129 B2
APPLICATION NO. : 15/191648
DATED : February 4, 2020
INVENTOR(S) : Kunal Virendra Gujraty et al.

It is certified that error appears in the above-identified patent and that said Letters Patent is hereby corrected as shown below:

On the Title Page

Below Item (65) insert:
--Related U.S. Application Data
(63) Continuation of PCT/US14/71053 filed December 18, 2014.
(60) Provisional application No. 61/920,471 filed December 24, 2013.--

Signed and Sealed this
Twenty-first Day of April, 2020

Andrei Iancu
*Director of the United States Patent and Trademark Office*